(12) United States Patent
Eguchi et al.

(10) Patent No.: US 7,790,175 B2
(45) Date of Patent: Sep. 7, 2010

(54) STRAIN OF TURKEY TAIL MUSHROOM, EXTRACT FROM THE SAME, AND USE OF THE SAME

(75) Inventors: Fumio Eguchi, Takasaki (JP); Ryo Sumi, Hashima (JP); Nobuo Mori, Hashima (JP)

(73) Assignee: Nikken Sohonsha Corporation, Hashima, Gifu (JP)

( * ) Notice: Subject to any disclaimer, the term of this patent is extended or adjusted under 35 U.S.C. 154(b) by 425 days.

(21) Appl. No.: 11/996,961

(22) PCT Filed: Jul. 28, 2006

(86) PCT No.: PCT/JP2006/314978

§ 371 (c)(1),
(2), (4) Date: Jan. 26, 2008

(87) PCT Pub. No.: WO2007/013588

PCT Pub. Date: Feb. 1, 2007

(65) Prior Publication Data

US 2010/0047269 A1    Feb. 25, 2010

(30) Foreign Application Priority Data

Jul. 28, 2005    (JP) .............................. 2005-218554

(51) Int. Cl.
*A61K 36/09*    (2006.01)
(52) U.S. Cl. ................................. 424/195.15
(58) Field of Classification Search ........................ None
See application file for complete search history.

(56) References Cited

U.S. PATENT DOCUMENTS 5,008,243 A    4/1991    Ikuzawa et al.

2002/0176796 A1 * 11/2002 Holloway et al. ............. 422/24
2005/0180991 A1 * 8/2005 Matsunaga ............. 424/195.15
2006/0246581 A1 * 11/2006 Tomita .................... 435/304.1

OTHER PUBLICATIONS

Japanese Patent Abstract Publication No. 08-113540 published Jul. 5, 1996, one page.
Japanese Patent Abstract Publication No. 11-060495 published Feb. 3, 1999, one page.
Japanese Patent Abstract Publication No. 2004-075640 published Nov. 3, 2004, one page.
International Search Report for PCT/JP2006/314978, mailed Aug. 22, 2006, three pages.

* cited by examiner

*Primary Examiner*—Christopher R Tate
*Assistant Examiner*—Deborah A. Davis
(74) *Attorney, Agent, or Firm*—Rankin, Hill & Clark LLP

(57) ABSTRACT

The present invention provides a new strain of turkey tail mushroom (*Trametes versicolor* (L.: Fr.) Pilat) having excellent biological activities (Accession number: FERM BP-10633). The strain is excellent in platelet aggregation inhibitory effect, chemokine gene expression inhibitory effect, antimutagenic effect, antitumor effect, antihypertensive effect, and immunomodulatory effect. The effect of the strain is enhanced synergistically by combining with microalgae and other basidiomycetes. The turkey tail mushroom of the present invention has high safety, and a possibility that a side effect is caused because of long-term continuous use is very low. Thus, it is useful for food/drink, cosmetics, pharmaceuticals or the like, the objective of which is the prevention and improvement in inflammation, allergy, tumor, and other diseases. The turkey tail mushroom strain of the present invention has very high hyphal growth property and very high physiological functions compared with conventional strains; therefore, it can be used stably.

18 Claims, 8 Drawing Sheets

STRAIN OF TURKEY TAIL MUSHROOM, EXTRACT FROM THE SAME, AND USE OF THE SAME

RELATED APPLICATIONS

This application claims the priority of Japanese Patent Application No. 2005-218554 filed on Jul. 28, 2005, which is incorporated herein by reference.

FIELD OF THE INVENTION

The present invention relates to a strain of turkey tail mushroom (*Trametes versicolor* (L.: Fr.) Pilat), an extract thereof, and applications thereof, and in particular, relates to a strain of turkey tail mushroom that is excellent in biological activities such as a platelet aggregation inhibitory effect, chemokine gene expression inhibitory effect, antimutagenic effect, antitumor effect, and antihypertensive effect.

BACKGROUND OF THE INVENTION

Mushrooms have been used not only for food but also for medicine, and mushrooms with various medicinal benefits have been known. Among them, turkey tail mushroom is called "yun zhi" in Chinese medicine, and it allegedly has antitumor activity. In addition, an antitumor agent (common name: PSK, trade name: Krestin) that was developed from a protein polysaccharide derived from turkey tail mushroom has been clinically used.

In recent years, its selective binding to TGF-β and PDGF (patent literature 1), its preventive effect on cancer and infection by administering it to immune system immature animals (patent literature 2), and its inhibitory effect on preadipocyte differentiation (patent literature 3) have been reported.

However, the medicinal benefits of turkey tail mushroom have not completely been clarified. In addition, a strain with better effects, for the already-known effects, has been sought-after.

Patent Literature 1: Japanese Unexamined Patent Publication No. H08-113540
Patent Literature 2: Japanese Unexamined Patent Publication No. H11-60495
Patent Literature 3: Japanese Unexamined Patent Publication No. H2004-75640

DISCLOSURE OF THE INVENTION

Problem to be Solved by the Invention

The present invention was made in view of the above-described problem of the conventional art, and an object is to provide a new strain of turkey tail mushroom with outstandingly useful activities and to provide applications thereof.

Means to Solve the Problem

In order to achieve the above-described object, the present inventors have diligently studied by repeating hybridization breeding of commercial and wild turkey tail mushrooms. As a result, the present inventors have succeeded to obtain a strain of turkey tail mushroom that is particularly excellent in the platelet aggregation inhibitory effect, chemokine gene expression inhibitory effect, antimutagenic effect, antitumor effect, antihypertensive effect, and immunomodulatory effect. In addition, the present inventors found that these effects could synergistically be enhanced by combining this turkey tail mushroom with microalgae or other basidiomycetes, thus leading to completion of the present invention.

The strain of the present invention is a strain of turkey tail mushroom (*Trametes versicolor* (L.: Fr.) Pilat), wherein the accession number is FERM BP-10633.

The platelet aggregation inhibitor, chemokine gene expression inhibitor, antimutagenic agent, antitumor agent, antihypertensive agent, and immunomodulatory agent of the present invention comprise the above-mentioned turkey tail mushroom and/or its extract as an active component.

The above-mentioned turkey tail mushroom and/or its extract can be blended into an oral composition such as a food, drink or a pharmaceutical composition.

The above-mentioned turkey tail mushroom and/or its extract can be blended into a skin external composition such as a cosmetic or a pharmaceutical external preparation.

In the present invention, it is desirable to use one or more selected from the group consisting of microalgae, other basidiomycetes, and these extracts in combination with the above-mentioned turkey tail mushroom and/or its extract.

Effect of the Invention

The specific turkey tail mushroom and/or its extract of the present invention have an excellent platelet aggregation inhibitory effect, chemokine gene expression inhibitory effect, antimutagenic effect, antitumor effect, antihypertensive effect, and immunomodulatory effect. In addition, these effects can synergistically be enhanced by combining with microalgae and other basidiomycetes. The turkey tail mushroom of the present invention has high safety, and a possibility that a side effect is caused because of long-term continuous use is very low. Thus, it is useful for food/drink, cosmetics, pharmaceuticals or the like, the objective of which is the prevention and improvement in inflammation, allergy, tumor, and other diseases. In addition, the turkey tail mushroom strain of the present invention has very high hyphal growth property and very high physiological functions compared with conventional strains; therefore, it can be used stably.

BEST MODE FOR CARRYING OUT THE INVENTION

Figure 1:
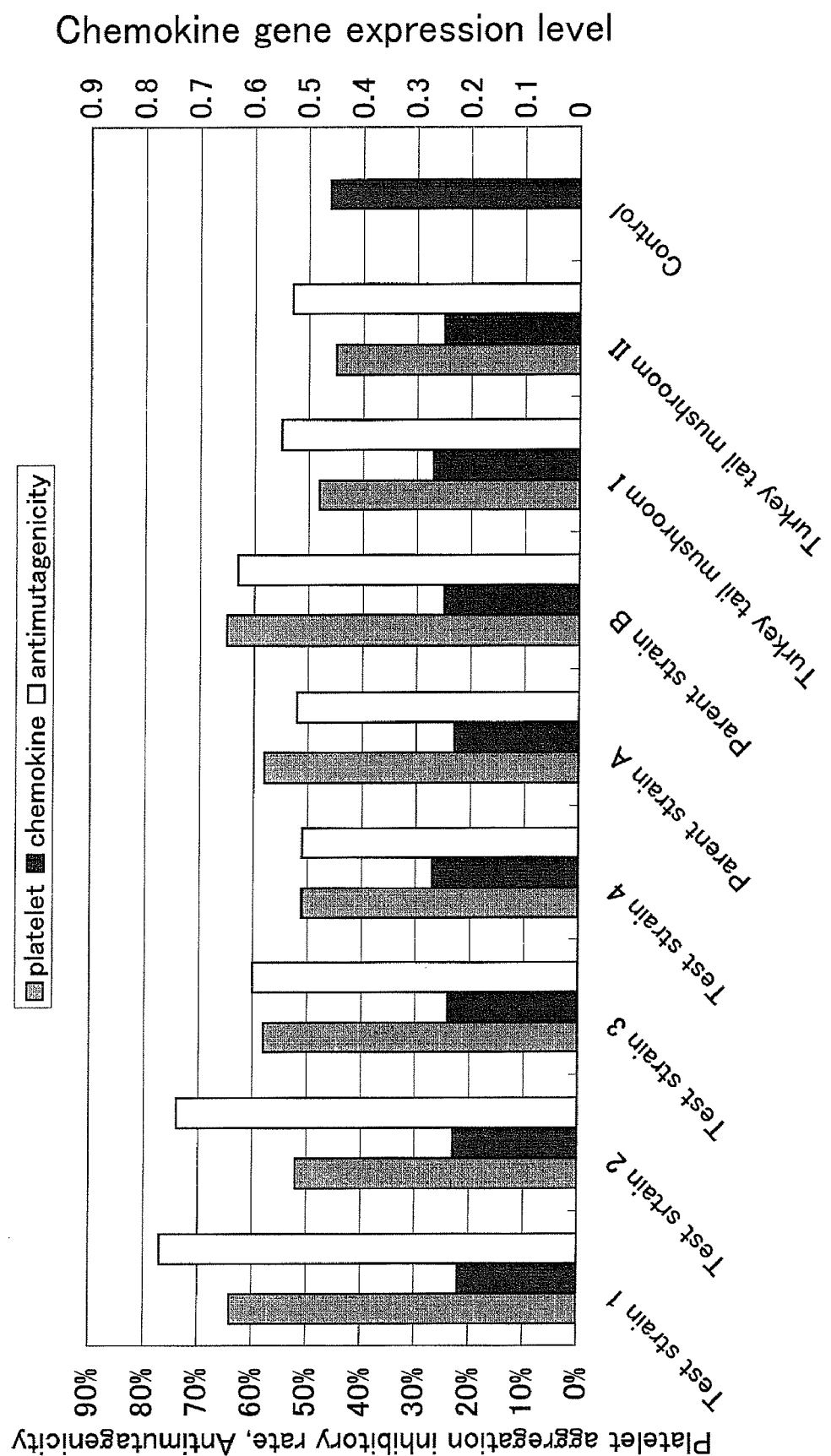
FIG. 1 shows a comparison in the platelet aggregation inhibitory effect, chemokine gene expression inhibitory effect, and antimutagenic effect of the carpophore hot water extract among the strain of turkey tail mushroom (test strain 1, FERM BP-10633) of the present invention, other created hybrid strains (test strains 2 to 4), parent strain A and parent strain B used for the creation of the test strains, and conventional strains, namely turkey tail mushroom I and turkey tail mushroom II (DMSO was used as a control).

Turkey tail mushroom (kawaratake) used in the present invention is *Trametes versicolor* (L.: Fr.) Pilat, which belongs to the genus *Coriolus* of the family Polyporaceae. The strain of turkey tail mushroom of the present invention was internationally deposited to the International Patent Organism Depositary of the National Institute of Advanced Industrial Science and Technology and accepted on Jun. 28, 2006, with the accession number of FERM BP-10633 (TANAKAY-OSHIHO™ strain). This international deposit was made by transfer from the domestic deposit thereof to the above Depositary with the accession number of FERM P-20377 (accepted on Jan. 26, 2005). The domestic and international deposits were made by EGUCHI Fumio, who is one of the present inventors.

This strain of turkey tail mushroom is a new strain of turkey tail mushroom obtained, by hybridization breeding using protoplast technology, from a wild turkey tail mushroom grown naturally in Kumamoto Prefecture, Japan. Compared with the conventional strains and parent strains, this strain has the highest activities in the hyphal growth, physiological functions, platelet aggregation inhibitory effect, chemokine gene expression inhibitory effect, antimutagenic effect, and antitumor effect. In addition, this strain has also high activity in antihypertensive effect and immunosuppressive effect. The creation method, selection method and effects of this strain are described in detail in Examples.

Here, the scientific characteristics and other information of the turkey tail mushroom strain of accession number FERM BP-10633 in accordance with the present invention are as follows.

1. Scientific Characteristics
   Characteristics of fungus: white colonies are formed in nutrient culture medium containing a carbon source and a nitrogen source. In addition, clamp connections are observed through an optical microscope.

2. Taxonomic Position
   Basidiomycete

3. Culture Condition
   (1) Name of Culture Medium
      SMYA culture medium (S: saccharose, M: malto extract, Y: yeast extract, A: agar)
      S and A: commercially available M and Y: made by Difco Corporation
   (2) Culture Medium Composition (per 1000 ml of culture medium)

| | |
|---|---|
| 1% saccharose | (10 g) |
| 1% malto extract | (10 g) |
| 0.4% yeast extract | (4 g) |
| 2% agar | (20 g) |

(3) pH of Culture Medium: 5.0-7.0 (optimal pH is 5.5)
   (4) Condition for Sterilizing Culture Medium: at 121° C., for 20 minutes
   (5) Temperature of Culture Medium: at 28° C.
   (6) Culture Period: for 10 days
   (7) Oxygen Requiring Property: aerobic 4. Storage Condition
   A Freezing method can be used for storage.
   (1) Freezing Condition: at −80° C.
   (2) Protective Agent: 10-20% glycerin aqueous solution (20% is optimal)
   (3) Restoration Ratio after Freezing: 100% after one year, 99% after three years 5. Conditions for Survival Test
   (1) Restoration of Microorganisms: at 40° C.
   (2) Methods for Inoculation, Culture and Confirmation: same as the Culture Condition In the present invention, a carpophore of the turkey tail mushroom, an extract of the carpophore, or dried material of the extract can be used. The carpophore can be either raw or dry; however, a dried carpophore is desirable from the standpoint of handling, storage stability, extraction efficiency, etc. In order to efficiently ingest an effective amount, it is preferable to use the dried powder of the carpophore or its extract, and it is more preferable to use the extract.

In the present invention, a carpophore is desirably used; however, its mycelium can also be expected to be effective. Raw mycelium that can be obtained by culturing a seed strain in a medium containing a carbon source and a nitrogen source or the dried mycelium can be used. The dried mycelium is easy to use.

It is desirable to break down the tissues of turkey tail mushroom prior to obtaining a turkey tail mushroom extract. In this way, the extraction can be efficiently carried out. As means for breaking down the tissues of turkey tail mushroom, there are physical treatments such as grinding treatment with various grinding mixers such as a bead mill, Waring blender, and homogenizer, impact crushing treatment with a blasting machine etc., a freezing treatment, and an ultrasonic treatment; and there are chemical treatments such as alkaline treatment with an aqueous solution of sodium hydroxide etc., a treatment with cell-wall degrading enzymes such as cellulase and pectinase, and an osmotic pressure treatment. These means can be used independently or in a suitable combination. Among these tissue destruction treatments, the grinding treatment or enzyme treatment is desirable when the carpophore of turkey tail mushroom is used as the raw material, and the enzyme treatment is desirable when mycelium is used as the raw material.

In the enzyme treatment, known cell-wall degrading enzymes or polysaccharide degrading enzymes can be used. One or more selected from the group consisting of cellulase, hemicellulase, chitinase, α- and β-glucuronidase, pectinase, xylanase, α- and β-glucanase, etc. can be used. For the enzyme treatment of turkey tail mushroom, an aqueous solution of an enzyme is added to suitably chipped or grounded turkey tail mushroom, and the mixture is shaken or stirred.

In order to obtain the turkey tail mushroom extract of the present invention, an extraction solvent is added to the turkey tail mushroom, the tissues of which have been broken down as described above, with suitable agitation to carried out the extraction.

The extraction solvent is not limited in particular; examples thereof include water; primary alcohols such as methanol and ethanol; polyhydric alcohols such as 1,3-butylene glycol and propylene glycol; lower alkyl esters such as ethyl acetate; hydrocarbons such as benzene and hexane; ethyl ether; acetone; and a combination of two or more of these. Examples of the desirable extraction solvents include water, methanol, ethanol, 1,3-butylene glycol, and a mixed solvent thereof. A hot water extract from the dried carpophore powder of turkey tail mushroom is especially desirable.

The extraction can be carried out at ordinary pressure and at ordinary temperature; however, it may also be carried out under a pressure of 1 to 5 atmospheres and on heating at 60 to 150° C. Specifically, it is desirable, for example, to carry out the extraction with hot water, and then to separate the extract solution and the residue by centrifuging or by filtration under reduced pressure.

The extraction from the extraction residue may be repeated several times under the same conditions as above.

The extract can be an extract solution or its dried material. In order to obtain dried material, the extraction solvent is removed from the extract solution by a treatment such as concentration under reduced pressure, sterilization, freeze drying, or spray drying.

The mycelial elongation of turkey tail mushroom is the best in the vicinity of 27° C. For the development of carpophores, a low temperature treatment within the range of 10 to 12° C. is suitable. For cultivation, the hyphal proliferation takes 20 to 25 days, and the subsequent carpophore development takes about 20 days. By the bag cultivation of 2.5 kg capacity, about 200 g of harvest is expected. Most broad-leaved trees are suitable as the sawdust used as a medium base, and even water-added cedar sawdust pile is usable.

Because the strain of turkey tail mushroom of the present invention is excellent in the platelet aggregation inhibitory effect and chemokine gene expression inhibitory effect, it is useful for the prevention or improvement of clot formation, improvement in blood flow, and the prevention or improvement of inflammatory or allergic diseases. When it is percutaneously administered as an external skin preparation, the prevention or improvement of inflammatory or allergic skin diseases can be expected.

The strain of turkey tail mushroom of the present invention is also excellent in the antimutagenic effect and antitumor effect. In the environment, there are various mutagenic compounds, and the damage to DNA in the body by these mutagenic compounds is considered to be one of the causes of cancer and other diseases. Accordingly, the strain of turkey tail mushroom of the present invention, which can inhibit mutagenic activity, is useful for the prevention of such diseases. It is also useful for the growth inhibition of tumor cells.

In addition, the strain of turkey tail mushroom of the present invention has antihypertensive effect, and the hypertension can be improved.

In addition, the strain of turkey tail mushroom of the present invention can balance the immune system in the body and contribute to the prevention of diseases and the maintenance of a healthy body because it has an immunomodulatory effect.

When the strain of turkey tail mushroom of the present invention is orally ingested, the necessary amount is different individually and it is not particularly limited; however, as the turkey tail mushroom extract (dry weight), 0.001 to 1 g per adult (60 kg body weight) per day can be used, and preferably 0.01 to 0.5 g.

It has become clear that the activity can synergistically be enhanced by combining at least one selected from the group consisting of microalgae, other basidiomycetes, and their extracts, together with the turkey tail mushroom of the present invention and/or its extract.

As the microalgae, those of the genus *Chlorella* can desirably be used, and in particular, *Chlorella pyrenoidaosa* can desirably be used; however, the microalgae are not limited to these.

As other basidiomycetes, at least one selected from the group consisting of agaricus (*Agaricus blazei*), meshimakobu (*Phellinus linteus*), shiitake (*Lentinus edodes*), and plant worms (*Cordyceps sinensis*) can desirably be used.

The extraction of these microalgae and basidiomycetes can be carried out according to the above-described extraction method for turkey tail mushroom or other known methods.

It has been reported that some of the above-described microalgae and basidiomycetes have antitumor activity; however, when they are used in combination with the turkey tail mushroom of the present invention, the activity can synergistically be enhanced compared with when they are used independently. The synergistic enhancement has also been observed in the platelet aggregation inhibitory effect, chemokine gene expression inhibitory effect, and antimutagenic effect.

The mixing ratio of the two are not limited in particular, the ratio of the turkey tail mushroom and/or its extract to the sum of microalgae, other basidiomycetes and these extracts is preferably within the range from 1:1 to 25:1 in the weight ratio, and more preferably from 5:3 to 15:1.

When oral compositions are prepared with the turkey tail mushroom or its extract of the present invention, powder, tablet, capsule, granule, medicinal tea, suspension, fluid extract, liquid preparation, syrup, etc. can be prepared according to the normal methods. In the formulation, normal formulation carriers, for example, excipient, binder, disintegrator, lubricant, colorant, flavoring, perfume, etc. can be used as necessary. In addition, coating can be applied, as necessary, with suitable coating agents.

The turkey tail mushroom or its extract of the present invention can be ingested as functional food, health food, and supplements in addition to pharmaceuticals. These can be ingested, for example, in the form of jelly, candy, gummy, cracker, juice, and various other forms.

For the production of an external skin preparation, the turkey tail mushroom extract is simply blended into a normally known base for external skin preparations. In the external skin preparations of the present invention, the components normally used in external skin preparations such as cosmetics and drugs can be suitably blended, as necessary, in addition to the above-described essential components. Their examples include whitening agents, moisturizers, antioxidants, preservatives, oil components, UV absorbers, surfactants, thickeners, alcohols, powder components, coloring material, perfume, aqueous components, water, polymer compounds, chelating agents, pH adjusters, vitamins, amino acids, and various skin nutrients and drugs.

External skin preparations can be applied to drugs, quasi-drugs, and cosmetics. Their forms are not limited in particular so far as they have conventionally been used in the external skin preparations. Their examples include ointment, cream, milky emulsion, lotion, pack, bath agent, sheet-type preparation, mousse, spray, and stick.

The blending quantity of the turkey tail mushroom into these oral compositions or skin external preparations can be suitably decided depending upon purposes and applications. Normally, as the turkey tail mushroom extract (dry weight), it is 0.0001 weight % or more in the composition, preferably 0.001 to 20 weight %, and more preferably 0.01 to 10 weight %.

The present invention will hereinafter be described by specific examples; however, the present invention is not limited by these examples.

EXAMPLES

I. Strain of Turkey Tail Mushroom and its Extract

As described below, the strain of turkey tail mushroom FERM BP-10633 of the present invention was selected and adopted as the best strain (test strain 1), compared with conventional strains or parent strains, in the physiological/biochemical tests and pharmacological activity tests among the test strains obtained by a hybridization breeding method using protoplast technology.

I-1. Creation of Test Strains

The general hybridization breeding method for mushrooms was used for parent strain A1, which is the below-described spore-derived monokaryotic hypha, and parent strain B1, which is protoplast-derived monokaryotic hypha. The obtained dikaryotic mycelia were observed under a microscope, and multiple test strains (hybrid strains) were obtained.

(1) Preparation of Monokaryotic Hyphae (Parent Strain A1) Derived from Spores

Spores (monokaryotic) were aseptically harvested from wild turkey tail mushroom carpophore A grown naturally in Kikuchi-shi of Kumamoto Prefecture, and they were cultured in an overlay agar medium. The regenerated colony of monokaryotic hyphae was cultured, and it was used as a strain for hybridization (parent strain A1). The culture was carried out at 26±2° C. and at a relative humidity of 80% or higher.

(2) Preparation of Monokaryotic Hyphae (Parent Strain B1) Derived from Protoplast Dikaryotic mycelium was aseptically isolated from wild turkey tail mushroom carpophore B grown naturally in Kikuchi-shi of Kumamoto Prefecture.

This mycelium was cultured in an SMY agar medium (contains 1% sucrose, 1% malt extract, 0.4% yeast extract, and 2% agar) for 7 days. The obtained mycelium was punched out with a cork borer with an inner diameter of 5 mm. This was inoculated in 40 mL of an SMY liquid medium (contains 1% sucrose, 1% malt extract, and 0.4% yeast extract) in a 100 mL Erlenmeyer flask. After the stationary culture for 7 days, the mycelium was ground with a magnetic stirrer and a stir bar, and a mycelium suspension was prepared.

Into another SMY liquid medium, 2 mL of this suspension was inoculated, serial subculture was carried out every 3 days, and the mycelium for protoplast preparation was obtained. The culture was carried out at 26±2° C. and at a relative humidity of 80% or higher.

The Mycelium for the protoplast preparation was corrected by filtration with nylon mesh (pore size: 10 10 μm). Into 2 mL of 0.05 mol/L maleic acid buffer solution (pH 6.0) containing 2% Novozym-234 (Novo Industry A/S), 0.5% Zymolyase-20T (Seikagaku Corporation), 0.2% Chitinase (Sigma Chemical Co.) and 0.5 mol/L mannitol, 200 mg (fresh weight) of the above obtained mycelium was placed. Enzyme treatment (protoplast treatment) was carried out by shaking for 1 hour under the conditions of a shaking width of 40 mm, a shaking frequency of 70/min, and a shaking temperature of 28° C.

This treated liquid was filtered with Miracloth (Calbiochem Corporation), and the filtrate was centrifuged at 1100 g for 10 minutes. The obtained precipitate (protoplast) was washed three times with 0.05 mol/L maleic acid buffer solution (pH 6.0, contains an osmoregulator) by repeated centrifugation to obtain purified protoplast.

This purified protoplast was cultured in an overlay agar medium, monokaryotic hyphae were screened from the regenerated colony to obtain a strain for hybridization (parent strain B1).

I-2. Physiological/Biochemical Tests

In order to stably utilize the strains, it is important that the hyphal growth and the physiological function are high. Thus, a screening, in which the hyphal growth and the laccase activity are used as indicators, was carried out. Test methods are as follows.

(1) Hyphal Growth in Solid Medium

Respective mycelia were cultured in an SMY agar medium for 7 days. The obtained mycelium was punched out with a cork borer with an inner diameter of 5 mm. This was inoculated on 25 mL of new SMY agar medium, which was dispensed into a Petri dish with an inner diameter of 90 mm. The culture was carried out at a culture temperature of 26±2° C. and at a relative humidity of 80% or higher for 8 days. Then the mycelial growth (mm) and the hyphal density were measured with the naked eye (n=10). The hyphal density was evaluated with "high: ++++", "normal: +++", "low: ++", and "very low: +".

(2) Hyphal Growth in Liquid Medium

Respective mycelia were cultured in an SMY agar medium for 7 days. The obtained mycelium was punched out with a cork borer with an inner diameter of 5 mm. This was inoculated into 40 mL of SMY liquid medium placed in a 100 mL Erlenmeyer flask. The stationary culture was carried out at a culture temperature of 26±2° C. and at a relative humidity of 80% or higher for 21 days. Then the mycelium was corrected by filtration with filter paper, the constant weight of which had been weighed in advance. The filter paper with the mycelium was dried with a drier and the constant weight was weighed. The proliferated amount of the mycelium (mg) was calculated by a subtraction method (n=10).

(3) Laccase Activity

Mycelium is inoculated into SMY liquid medium containing 1 mM veratric acid and cultured for 13 days at a culture temperature of 26±2° C. and at a relative humidity of 80% or higher. The laccase activity (nkat/L) of the filtrate was measured with a spectrophotometer according to a conventional method (refer to "Mokuzai Gakkaishi", 40(1), 107-110 (1994)).

(4) Results

The test results are shown in Table 1.

Parent strain A1 and parent strain B1 are monokaryotic hyphae obtained according to the above methods.

Parent strain A2 and parent strain B2 are dikaryotic hyphae, and they were obtained, respectively, by the subculture of the original seed strains, which were isolated from turkey tail mushroom carpophore A and turkey tail mushroom carpophore B before the creation of parent strain A1 and parent strain B1.

Turkey tail mushroom I and turkey tail mushroom II are the isolates (dikaryotic hyphae) obtained from wild turkey tail mushrooms harvested in Takasaki-shi of Gunma Prefecture and in Okutama-machi of Tokyo Prefecture, respectively.

The test results showed that the hyphal growth and the physiological function of test strain 1 were especially high among the obtained multiple test strains (only test strains 1 to 4 are shown in Table 1) and that test strain 1 was superior to the parent strains and to the conventional strains.

utes to isolate platelet poor plasma (PPP). PRP (223 μL) was prewarmed at 37° C., and 2 μL of the powder from a hot water extract of the turkey tail mushroom (dissolved in DMSO so that the concentration is 2%) or 2 μL DMSO (control) was added, respectively. The incubation was carried out for 3 minutes at 37° C.; then 25 μL of sodium arachidonate aqueous solution (500 nM), which is aggregation-inducing material, was added.

The induced aggregation was measured with an aggregometer (MCM Hematracer, MC Medical Inc.). The maximum aggregation rate (maximum value obtained from an aggregation curve of the test sample assuming the value for PPP is 100) for the test sample and the maximum aggregation rate of the control were compared, and the aggregation inhibitory effect of the test material against the platelet aggregation induced by sodium arachidonate aqueous solution was evaluated.

(3) Test for the Inhibition of Chemokine Gene Expression

Human skin fibroblast was cultured, in a culture plate with a diameter of 6 cm, with DMEM medium (Dulbecco's Modi-

TABLE 1

| Strain | Hyphal growth (Solid medium, mm) | Hyphal density (Solid medium) | Hyphal growth (Liquid medium, mg) | Laccase activity (nKat/L) |
|---|---|---|---|---|
| Test strain 1 | 85.6 ± 3.1 | ++++ | 351 ± 21 | 189.7 |
| Test strain 2 | 82.4 ± 2.4 | +++ | 288 ± 33 | 147.5 |
| Test strain 3 | 85.8 ± 2.1 | +++ | 297 ± 18 | 155.4 |
| Test strain 4 | 79.8 ± 6.1 | +++ | 198 ± 36 | 171.3 |
| Parent strain A1 | 71.6 ± 3.6 | ++ | 158 ± 55 | 142.3 |
| Parent strain B1 | 61.3 ± 2.9 | ++ | 207 ± 44 | 138.6 |
| Parent strain A2 | 81.2 ± 3.3 | +++ | 324 ± 27 | 158.7 |
| Parent strain B2 | 80.9 ± 2.7 | +++ | 298 ± 32 | 169.1 |
| Turkey tail mushroom I | 83.6 ± 3.1 | +++ | 257 ± 35 | 154.2 |
| Turkey tail mushroom II | 81.4 ± 2.8 | ++++ | 328 ± 17 | 138.6 |

I-3. Pharmacological Activity Test

The test for platelet aggregation inhibition, the test for inhibition of chemokine gene expression, and antimutagenicity test were conducted.

(1) Preparation of Powder from a Hot Water Extract of the Turkey Tail Mushroom

Fine powder (40 g) of the dried carpophores of turkey tail mushroom and 750 mL of distilled water were mixed, and the extraction was carried out, with stirring, at 90° C. for 1 to 2 hours. Then the mixture was centrifuged (3000 rpm, 15 minutes), and the collected supernatant was concentrated with an evaporator (about 10 times). The concentrate was frozen at −80° C., and freeze-dried to obtain 3.5 g of the powder from a hot water extract of the turkey tail mushroom; this was used as a test sample.

In addition to test strains 1 to 4, respective carpophores of turkey tail mushroom carpophore A and turkey tail mushroom carpophore B, which are parent strains, and turkey tail mushroom I (harvested in Takasaki-shi in Gunma Prefecture) and turkey tail mushroom II (harvested in Okutama-machi in Tokyo Prefecture) were similarly treated to prepare respective hot water extract powders, and they were used as test samples.

(2) Test for Platelet Aggregation Inhibition

Human blood was centrifuged at 1100 rpm for 20 minutes at room temperature to isolate platelet rich plasma (PRP). Then, the centrifuging was continued at 3000 rpm for 5 minfied Eagle's Medium) containing 10% fetal calf serum until the cells reach confluence; thus a test medium for the experiment was obtained.

To the test medium, the powder from a hot water extract of the turkey tail mushroom (dissolved in a suitable amount of DMSO), DMSO (negative control), or hydrocortisone (positive control) was added. The final concentrations of the powder from a hot water extract of the turkey tail mushroom and DMSO were 0.01% (dry weight), respectively. The final concentration of hydrocortisone was $10^{-7}$ M.

Then tumor necrosis factor TNF-α (1 ng/mL), which is known to promote chemokine gene expression, was added, and the culture was carried out at 37° C. for 6 hours.

Subsequently, RNA was isolated from the cell by the conventional method, cDNA was synthesized, and the expression level of IL-8 gene was measured by the quantitative PCR method (TaqMan PCR method). Here, GAPDH (glyceraldehyde-3-phosphate dehydrogenase) gene was used as the internal standard gene to correct the obtained data.

Human skin fibroblast is commercially available; for example, it is available from Kurabo Industries Ltd. Human fibroblast can be cultured by the conventional method for the culture of animal cells, and in particular, DMEM medium containing 10% fetal calf serum is desirable.

(4) Antimutagenicity Test

In a test tube, 0.1 mL of mutagen (DMSO solution containing 0.2 M 2-amino-3-methylimidazo[4,5-f]quinoline) and 1.9 mL of the powder from a hot water extract of the turkey tail mushroom (dissolved in DMSO so that the concentration is 0.25 to 1%, 1% in the figures and tables below) were mixed, and the mixture was allowed to stand at 37° C. for 6 hours.

Then, 0.1 mL of a *salmonella* strain TA98 solution (His+ revertants, added to DMSO so that the concentration is 5 to 7%, 7% in the figures and tables below), 0.5 mL of S9 mix, and 2 mL of soft agar were added into this test tube and mixed.

Into a minimal glucose agar medium, 0.05 mL of this mixed solution was seeded, and the culture was carried out at 37° C. for 48 hours. The number of proliferated histidine-independent colonies was counted, and the antimutagenicity (%) was calculated with the following equation.

Antimutagenicity (%)=[(*NC*−*NB*)−(*NS*−*NB*)]/(*NC*−*NB*)100

NS: number of colonies when a sample solution was added
NC: number of colonies when DMSO was added instead of a sample solution (control)
NB: number of colonies when DMSO was added instead of a sample solution and mutagen (blank)

(5) Results

The results are shown in FIG. 1. As seen from FIG. 1, test strain 1 had very high activity in the platelet aggregation inhibitory effect, inhibitory effect of the expression level of chemokine (IL-8) gene, and antimutagenic effect, and test strain 1 was excellent compared with other test strains, parent strains, and conventional strains.

It is gradually being clarified that arachidonic acid and its metabolites, leukotrienes, thromboxane, and prostaglandins are involved in the occurrence of various inflammatory or allergic skin diseases and skin roughness. For example, in psoriasis, which is inflammatory dyskeratosis, a high concentration of arachidonic acid metabolites is observed to be present at the diseased epidermis. In atopic dermatitis, which is an allergic skin disease, contact dermatitis, and eczema, an involvement of arachidonic acid metabolites has been suggested. Because prostaglandins and thromboxanes allow the aggregation of platelets, a compound that inhibits the synthesis of prostaglandins and thromboxanes from arachidonic acid is considered to have an antithrombotic effect, namely, a blood flow improving effect.

In recent years, it has been gradually clarified that chemokine (chemotactic cytokine), which controls the migration and activation of inflammatory cells, is deeply involved in the occurrence of various inflammatory and allergic skin diseases. Chemokine is a generic name for heparin binding basic proteins with a molecular weight of 8 to 10 kDa. It is considered that in the body, chemokine mainly acts on the migration of various inflammation cells to inflammation sites and the activation of those cells, and plays an important role in the induction of inflammation.

In skin diseases, inflammatory cells such as neutrophils and eosinophils migrate to inflammation sites of contact dermatitis, atopic dermatitis, etc. and become active, and they are considered to be involved in the occurrence and exacerbation of inflammation. It is known, in this case, that chemokines such as interleukin-8 (IL-8) are generated from cells such as keratinocytes of the skin and fibroblasts. It is also known that IL-8 is present in large quantities at a diseased skin area of psoriasis, which is inflammatory dyskeratosis.

Accordingly, the inhibition of expression of chemokines such as IL-8 is considered to be effective for the improvement or prevention of symptoms of these inflammatory or allergic diseases.

In the environment, there are various mutagenic compounds, and the damage to DNA in the body by these mutagenic compounds is considered to be one of the causes of cancer and other diseases. Accordingly, antimutagenic materials that can inhibit the mutagen activity are useful for the prevention of such diseases.

I-4. Safety Testing

An acute toxicity test and a subacute toxicity test were conducted to investigate the safety of test strain 1, which was the best in the growth, physiological functions, and activity, trough the above test.

(1) Test Method (a) Acute Toxicity

An acute oral toxicity test was conducted with mice (n=10) according to the OECD Guidelines for the toxicity testing of chemical substances (1987). As a test sample, the powder obtained from a hot water extract of the turkey tail mushroom was used. The dosage was 200, 400, 600, 800, or 2000 mg/kg, and a single administration was given. The observation of the individuals was conducted for 24 days after administration.

(b) Subacute Toxicity

A subacute toxicity test (oral administration) was conducted with mice (n=10) according to the OECD Guidelines for the toxicity testing of chemical substances (1987). As a test sample, the powder obtained from a hot water extract of the turkey tail mushroom was used. The dosage was 200, 400, 600, 800, or 2000 mg/kg per day, and the administration was given once every day for 28 days.

(2) Results (a) Acute Toxicity

In the acute toxicity test of test strain 1, even at an oral dosage of 2000 mg/kg, no dead individual and no denaturalization of organs or blood were observed; thus, it was confirmed that test strain 1 had a high safety.

(b) Subacute Toxicity

In the subacute toxicity test of test strain 1, even at an oral dosage of 2000 mg/kg, no dead individual and no degeneration of organs or blood were observed; thus, test strain 1 was confirmed to have a high safety.

For example, hydrocortisone is known to be potent as a chemokine gene expression inhibitor. In the above-described inhibition test of chemokine gene expression, the gene expression level with hydrocortisone was 0.13, and hydrocortisone exhibited a high inhibitory effect. However, steroid hormones cause side effects such as inflammation, tissue damage, and ulcer formation when it is taken for a long time. On the other hand, the inhibitory effect of test strain 1 was not as high as that of hydrocortisone. However, test strain 1 is free of side effects and very safe; thus it is possible to take it for a long time.

I-5. Dual Culture Test

For test strain 1, dual cultures were carried out against parent strain A, parent strain B, and conventional strains, respectively. In this test, the homology of two strains can be easily judged by observing the formation of a zone line at the contacting surface of two facing colonies. The test was carried out as follows.

Wood powder of Japanese beech (*Fagus crenata* Blume) that passed a sieve with a diameter of 0.8 mm (20 mesh) and rice bran were mixed in a ratio of 5:1 (weight ratio). Then water was added to the mixture so that the water content would be 75%. This mixture was packed at the center of a glass tube with a length of 250 mm and a diameter of 30 mm, and it was sterilized with an autoclaved for 30 minutes under the conditions of 120° C. and 1.2 atmospheres. From both ends of this wood powder medium, respective strains were inoculated, and the culture was carried out at 26° C. and at a relative humidity of 75% or higher. The presence or absence of the zone line formation was observed with the naked eye.

As a result, test strain 1 formed a zone line against all parent strains and the conventional strains. Accordingly, the homology to them was low, and test strain 1 was considered to be a different from them.

Based on the above results, the present inventors selected this test strain 1 and domestically deposited this strain to the International Patent Organism Depositary of the National Institute of Advanced Industrial Science and Technology (accession number: FERM P-20377). This strain was further internationally deposited to the above Depositary (accession number: FERM BP-10633), by transfer from the domestic deposit. This strain was adopted as the turkey tail mushroom of the present invention.

Figure 2:
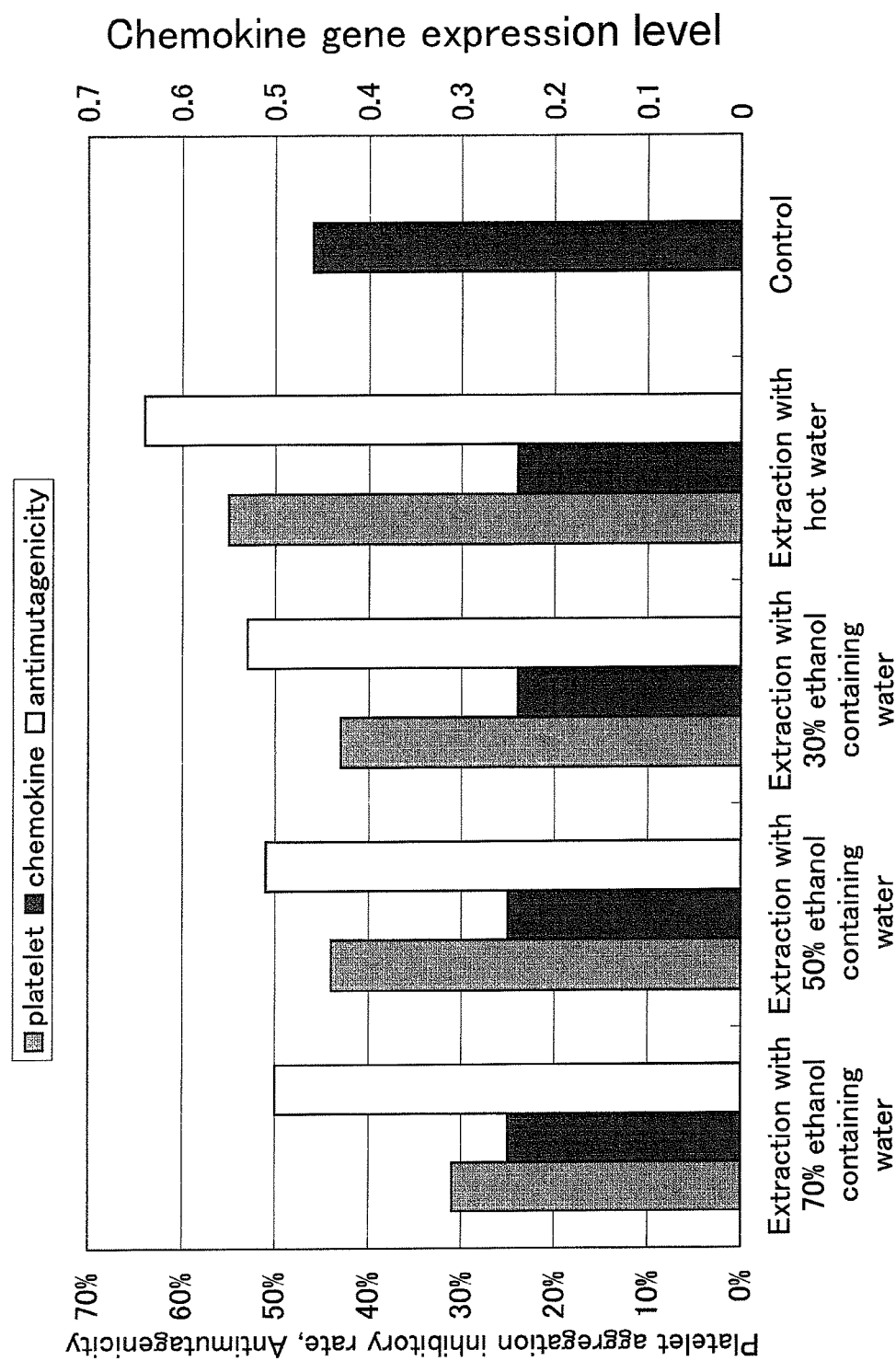
FIG. 2 shows a comparison in the platelet aggregation inhibitory effect, chemokine gene expression inhibitory effect, and antimutagenic effect among the hot water extract and hydrous ethanol extracts from the carpophore of the strain of turkey tail mushroom (test strain 1, FERM BP-10633) of the present invention (DMSO was used as a control).

FIG. 2 shows the results of the pharmacological activity tests for the powders prepared from the turkey tail mushroom extract, wherein the same method as the above-described method was used except that the extraction solvent was hydrous ethanol and the extraction temperature was room temperature (25° C.). As seen from FIG. 2, the extraction case with hot water exhibited the highest activity though the extraction case with hydrous ethanol also exhibited activity. In addition, the extraction with hot water showed a desirable trend in the recovery of extracted powder.

I-6. Antitumor Testing (in Vitro)

The antitumor effect of the strain of turkey tail mushroom FERM BP-10633 was tested with cultured sarcoma 180 cells.

(1) Preparation of Test Medium

The mixture of 87% MEM Earle liquid medium (without glutamine, with overlay; INC Biomedicals Inc.), 10% fetal calf serum (inactivated for 30 to 60 minutes at 56° C., GIBCO), 2% 200 mM glutamine solution (29.23 mg/mL: INC Biomedicals Inc), and 1% penicillin-streptomycin (10,000 unit/mL: GIBCO) was used as the test medium.

(2) Preparation of Sample Solution

Powder from a hot water extract of the turkey tail mushroom (FERM BP-10633) was diluted 1000 times with PBS and autoclave-sterilized, and the obtained solution was used as a sample solution. The similarly sterilized solution of PBS only was used as a control.

(3) Test Method

To each well of a 96-well plate, 180 μL of the test medium was dispensed; then 10 μL of sarcoma 180 tumor cell strain and 10 μL of the sample solution were added. The number of sarcoma 180 tumor cells was $5 \times 10^3$ cells/well (200 μL). The number of the cells was measured after being allowed to stand for 48 hours at 37° C. under 5% $CO_2$.

(4) Results

The results are shown in Table 2. The sample solution achieved a significant proliferation inhibitory effect against sarcoma 180 tumor cells. Accordingly, turkey tail mushroom FERM BP-10633 of the present invention is considered to have an antitumor effect.

TABLE 2

|  | Number of cells | | |
| --- | --- | --- | --- |
|  | Before culture | After culture | Growth ratio |
| Control (only PBS) | $5 \times 10^3$ | $5.2 \times 10^4$ | 10.4-fold |
| Sample solution | $5 \times 10^3$ | $1.2 \times 10^4$ | 2.4-fold |

I-7. Antitumor Testing (in Vivo)

The proliferation inhibitory effect of the strain of turkey tail mushroom FERM BP-10633 was tested in vivo against sarcoma 180 tumor cells.

(1) Test Method

As test animals, 24 four-week-old BALB/c-nu/nu (nude mouse) female mice were used. At 5 weeks old, sarcoma 180 tumor cells ($1 \times 10^6$ cells/0.05 mL) was implanted in the left abdominal area of each mouse. The test animals were separated into the following three groups for administration.

(i) Control group: forced oral administration of water (powder from a hot water extract of the turkey tail mushroom carpophore was not administered).

(ii) 50 mg/kg administration group: forced oral administration (every day from 5 weeks old) of 50 mg/kg (2 mg/0.2 mL per 40 g of mouse) per day of the powder from a hot water extract of the turkey tail mushroom carpophore (iii) 500 mg/kg administration group: forced oral administration (every day from 5 weeks old) of 500 mg/kg (20 mg/0.2 mL per 40 g of mouse) per day of the powder from a hot water extract of the turkey tail mushroom carpophore The tumor volume was measured every week after the sarcoma 180 tumor cells were implanted.

(2) Results

As shown in Table 3, the tumor growth was prominently inhibited in the test group (administration group) compared with the control group (non-administration group).

TABLE 3

|  | Tumor volume (mm³)* | | |
| --- | --- | --- | --- |
|  | 1-week later | 2-week later | 3-week later |
| Control group | 279.67 ± 114.97 (100%) | 1608.98 ± 559.22 (100%) | 5254.39 ± 1077.34 (100%) |
| 50 mg/kg - administration group | 153.88 ± 55.74 (55.02%) | 1012.58 ± 220.44 (62.93%) | 3860.59 ± 1046.93 (73.47%) |
| 500 mg/kg - administration group | 110.44 ± 66.07 (39.49%) | 792.22 ± 400.39 (49.24%) | 3076.94 ± 989.23 (58.56%) |

*tumor volume (mm³) = (major axis) × (minor axis)² × ½

II. Compositions Containing the Turkey Tail Mushroom Extract

As described above, the strain of turkey tail mushroom FERM BP-10633 of the present invention has very high activity. In order to further improve the activity, the combined use with microalgae or other basidiomycetes was also investigated.

II-1. Platelet Aggregation Inhibition Test, Test for the Inhibition of Chemokine Gene Expression and Antimutagenicity Test (1) Test 1

As test samples, *chlorella* extract powder, shiitake extract powder, and *chlorella* shiitake extract powder, which are (i) to (iii) described below, were used in addition to the powder from a hot water extract of the turkey tail mushroom (FERM BP-10633). The platelet aggregation inhibition test, test for the inhibition of chemokine gene expression, and antimutagenicity test were conducted in the same method as the above-described method.

Figure 3:
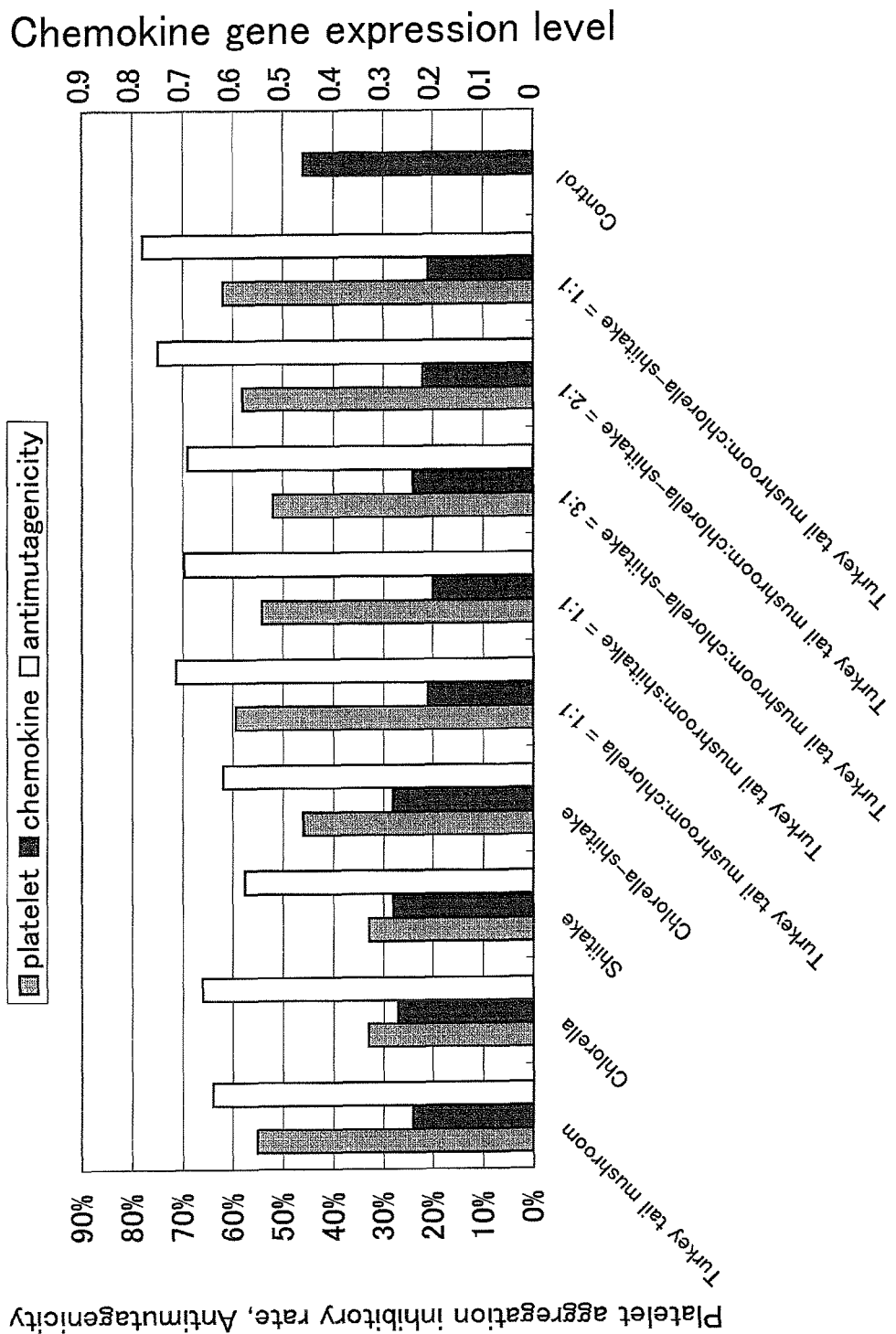
FIG. 3 shows a synergistic effect in the platelet aggregation inhibitory effect, chemokine gene expression inhibitory effect, and antimutagenic effect when a hot water extract from the carpophore of the strain of turkey tail mushroom (test strain 1, FERM BP-10633) of the present invention was mixed with a hot water extract from *chlorella* and/or shiitake carpophores (DMSO was used as a control).

As shown in FIG. 3, when the powder from a hot water extract of the turkey tail mushroom (FERM BP-10633) is used in combination with *chlorella* extract powder, shiitake extract powder, or *chlorella* shiitake extract powder, the platelet aggregation inhibitory test effect, inhibitory effect of chemokine gene, and antimutagenic effect were synergistically enhanced compared with the case in which each component was used independently. Especially when *chlorella* shiitake extract powder was mixed, these effects were prominent.

(i) Preparation of *chlorella* Extract Powder

Into a *chlorella* extraction tank, 40 kg of *chlorella* (*Chlorella pyrenoidosa*) and 750 L of distilled water were placed, the temperature was increased to 90° C., and the extraction was carried out for 30 minutes. Then, a supernatant was collected after centrifuging to obtain a *chlorella* extract.

This extract was concentrated to about 45 L (about 18 times) with an evaporator, and 40 kg of β-cyclodextrin was added to the concentrate. The mixture was dried, until the water content became 5% or less, by drum drying (surface temperature of the drum: about 150° C., reaction temperature: about 90° C.) while stirring with a kneader. About 50 kg of *chlorella* extract powder was obtained by crushing the dry chip-shaped material, which was generated in the dried product, with a pulverizer.

(ii) Preparation of Shiitake Extract Powder

Into a shiitake extraction tank, 40 kg of dry chip-shaped carpophores of shiitake (*Lentinus edodes*) and 750 L of distilled water were placed, the temperature was increased to 85° C., and the extraction was carried out for 60 minutes. Then an extract was collected by squeezing with a shiitake squeezer and it was further centrifuged. The supernatant was collected to obtain a shiitake extract.

This extract was concentrated to about 45 L (about 18 times) with an evaporator, and 40 kg of β-cyclodextrin was added to the concentrate. The mixture was dried, until the water content became 5% or less, by drum drying (surface temperature of the drum: about 150° C., reaction temperature: about 90° C.) while stirring with a kneader. About 50 kg of shiitake extract powder was obtained by crushing the dry chip-shaped material, which was generated in the dried product, with a pulverizer.

(iii) Preparation of *chlorella* Shiitake Extract Powder

The above *chlorella* extract (650 L) and shiitake extract (620 L) were mixed, and the mixture was concentrated to 70 L with an evaporator. To this concentrate, 27.5 kg of β-cyclodextrin was added. The mixture was dried, until the water content became 5% or less, by drum drying (surface temperature of the drum: about 150° C., reaction temperature: about 90° C.) while stirring with a kneader. About 40 kg of *chlorella* shiitake extract powder was obtained by crushing the dry chip-shaped material, which was generated in the dried product, with a pulverizer.

(2) Test 2

According to the below-described Formulation Examples 1 and 2, health drinks were prepared, and the testing was carried out by the same methods as the methods described above. As shown in Table 4, all health drinks exhibited very high activities in the platelet aggregation inhibitory effect, inhibitory effect of chemokine gene, and antimutagenic effect.

TABLE 4

|  | Platelet aggregation inhibition rate (%) | Chemokine gene expression level | Antimutagenicity (%) |
|---|---|---|---|
| Formulation Ex. 1 | 76.3 | 0.17 | 81.4 |
| Formulation Ex. 2 | 72.9 | 0.18 | 82.1 |

Formulation Example 1

Functional Health Drink (Contains the Below-Described Ingredients in 50 mL of Purified Water)

Powder from a hot water extract of the turkey tail mushroom (FERM BP-10633) 200 mg

| *Agaricus* hot water extract | 10 |
|---|---|
| *Shiitake mycelium* hot water extract | 10 |
| *Meshimakobu mycelium* hot water extract | 20 |
| Plant worms *mycelium* hot water extract | 10 |
| *Chlorella* extract | 200 |
| Carotenic 1% (milky emulsion containing 1% β-carotene) | 50 |
| Glycerin fatty acid ester | 100 |
| High-fructose corn syrup | 5000 |
| Honey | 1000 |
| *Hihatsu* (*Piper longum*) extract powder | 150 |
| Citric acid | 200 |
| Vitamin B6 | 10 |
| Flavoring | 200 |

Formulation Example 2

Functional Health Drink (Contains the Below-Described Ingredients in 50 mL of Purified Water)

Powder from a hot water extract of the turkey tail mushroom (FERM BP-10633) 200 mg

| *Agaricus* hot water extract | 10 |
|---|---|
| *Shiitake mycelium* hot water extract | 10 |
| *Meshimakobu mycelium* hot water extract | 20 |
| Plant worms *mycelium* hot water extract | 10 |
| *Chlorella* extract | 200 |

-continued

| | |
|---|---|
| Carotenic 1% (milky emulsion containing 1% β-carotene) | 50 |
| Glycerin fatty acid ester | 100 |
| High-fructose corn syrup | 5000 |
| Honey | 1000 |
| Green tea extract (catechin) | 500 |
| Citric acid | 200 |
| Vitamin B6 | 10 |
| Flavoring | 200 |

II-2. Antihypertensive Effect (SHR Model)

In vivo tests were carried out with the use of spontaneously hypertensive rats (SHRs (4 weeks old), procured from Charles River Laboratories Japan, Inc). At 7 to 15 weeks old, 100% of SHRs become spontaneously hypertensive. The blood pressure is about 171 mmHg on the average at 10 weeks old, and the maximum blood pressure reaches about 200 mmHg or higher. SHR mice also exhibit abnormal cholesterol metabolism and insulin resistance.

(1) Single Dose Test

To SHRs (10 weeks old, male), powder from a hot water extract of the turkey tail mushroom (FERM BP-10633), *chlorella* extract powder, or 1:1 mixture (weight ratio) thereof was orally administered, with a feeding needle, at a dose of 3.3 mg/kg as extract powder, and the blood pressure was monitored (n=6). Water was administered as a control. The average systolic blood pressures after 8 hours of the administration are shown in Table 5.

As shown in Table 5, a blood pressure-lowering effect was observed for each administration group, and the highest decrease in the blood pressure was observed for the administration group of the mixture.

TABLE 5

| Test sample | Average blood pressure |
|---|---|
| Turkey tail mushroom hot water extract powder | 187 ± 6 |
| *Chlorella* extract powder | 190 ± 4 |
| Mixture of 1:1 | 182 ± 8 |
| Control | 213 ± 7 |

To SHRs (10 weeks old, male), the health drink of the above-described Formulation Example 2 was orally administered, with a feeding needle, at a dose of 3.3 mg/kg as the powder obtained from a hot water extract of the turkey tail mushroom. The blood pressure was measured, with respect to time, immediately before the start of administration and for 48 hours after the administration (n=5).

Figure 4:
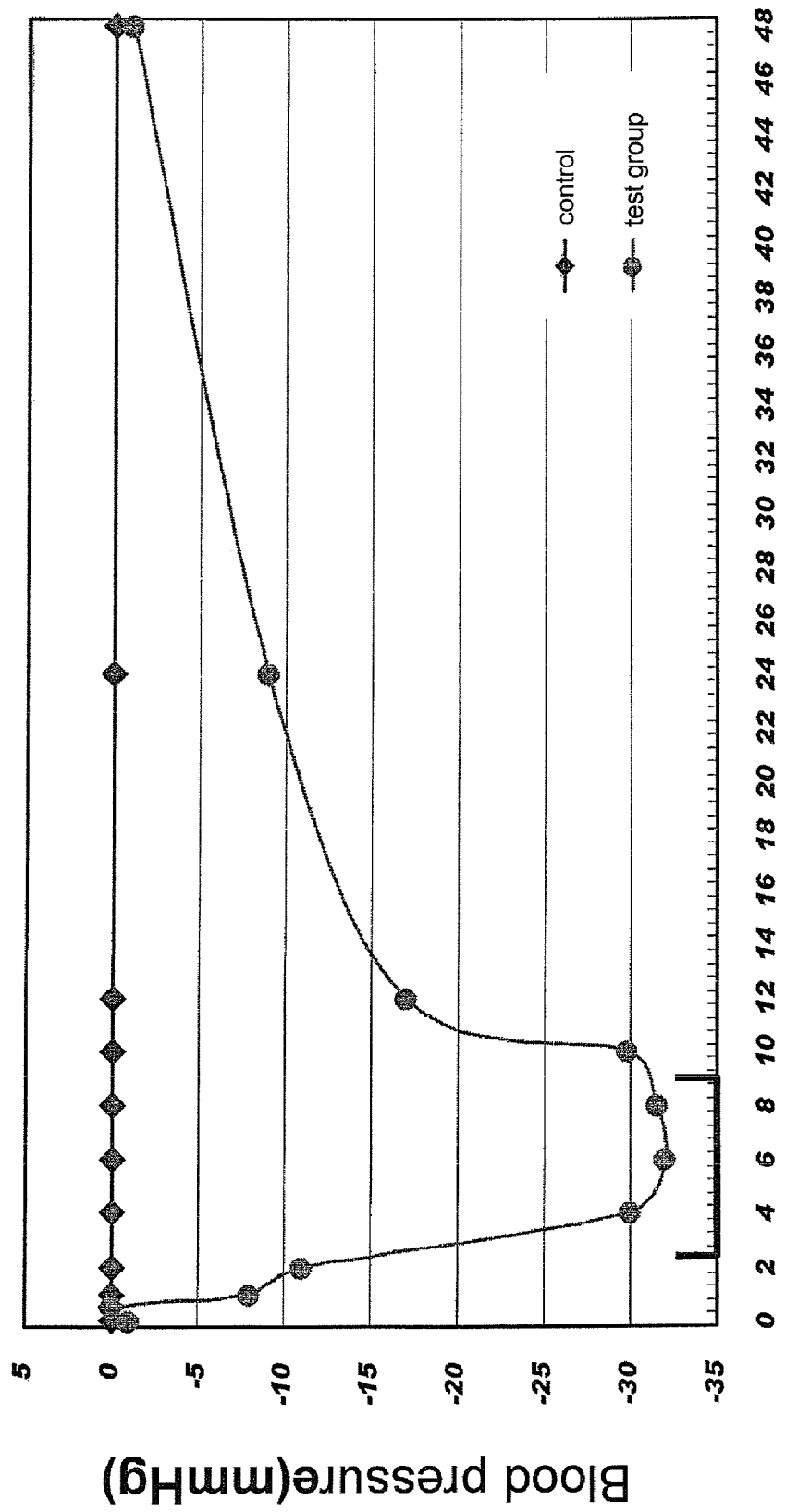
FIG. 4 shows a time-course change in the systolic blood pressure after a single administration, to SHRs, of a composition containing a hot water extract from the carpophore of the strain of turkey tail mushroom (test strain 1, FERM BP-10633) of the present invention with respect to the control (non-administration).

In FIG. 4, the average systolic blood pressure of the control group (non-administration group) was set at zero, and the average systolic blood pressure of the test group (administration group) was plotted. As seen from these results, the blood pressure of the test group started to decrease, relative to the control group, after 30 minutes of the administration. After 4 to 10 hours of the administration, the blood pressure decreased most. Then the blood pressure increased gradually; however, an increase was mild, and it took about 48 hours for the blood pressure to reach the same level as the control group.

(2) Chronic Administration Test

To SHRs (5 weeks old, male), the health drink of the above-described Formulation Example 2 was orally administered, with a feeding needle, at a dose of 3.3 mg/kg as the powder obtained from a hot water extract of the turkey tail mushroom. The administration was carried out once every day for 11 weeks until they become 16 weeks old. The blood pressure was measured immediately before the start of administration and immediately before each oral administration (n=5).

Figure 5:
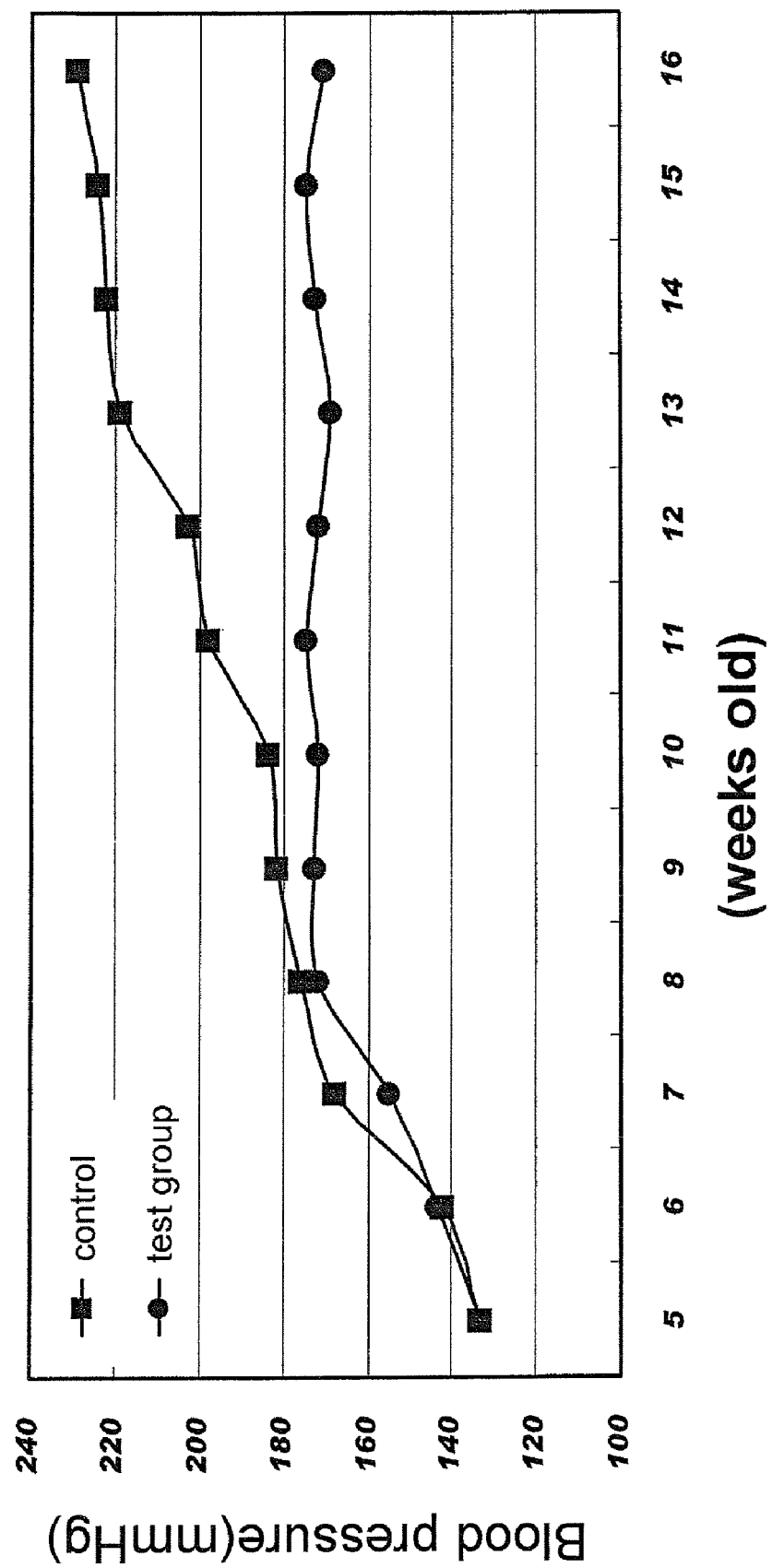
FIG. 5 shows a time-course change in the systolic blood pressure when a composition containing a hot water extract from the carpophore of the strain of turkey tail mushroom (test strain 1, FERM BP-10633) of the present invention was chronically administered to SHRs and when it was not administered (control).

In FIG. 5, the weekly variations of the average systolic blood pressure for the control group (non-administration group) and for the test group (administration group) are shown. The blood pressure of the control group gradually increased with an increase in weekly age. At 16 weeks old (after 11 weeks of administration), the blood pressure exceeded 220 mmHg. On the other hand, the blood pressure of the test group gradually increased until 8 weeks old (after 3 weeks of administration). Then the blood pressure stabilized and stayed in the range of 170 to 180 mmHg.

Thus, it was suggested that hypertension could be improved by the continual ingestion of the composition containing the turkey tail mushroom extract of the present invention and that the blood pressure could be controlled within a fixed range.

II-3. Antihypertensive Effect (Human)

The antihypertensive effect for hypertensive patients was clinically investigated.

(1) Test Method

The test subjects were 10 hypertensive patients (7 males and 3 females) that regularly had a systolic blood pressure of about 150 to 170 mm/Hg. The average systolic blood pressure of the test subjects was 162 mmHg, and the average diastolic blood pressure was 96 mmHg. These values were about the same for 10 days before the start of administration.

The subjects were requested to orally ingest the health drink of the above-described Formulation Example 2 once every day for 70 days from the starting day of administration (day zero). The amount of intake was 50 mL (200 mg as the powder obtained from a hot water extract of the turkey tail mushroom) per day. During the administration period, the blood pressure was measured immediately before each administration.

In addition, blood of the subject patients was collected into a blood collection tube containing a coagulation inhibitor, and the blood renin concentration and the blood angiotensin I concentration were measured according to the general clinical test methods.

(2) Results

Figure 6:
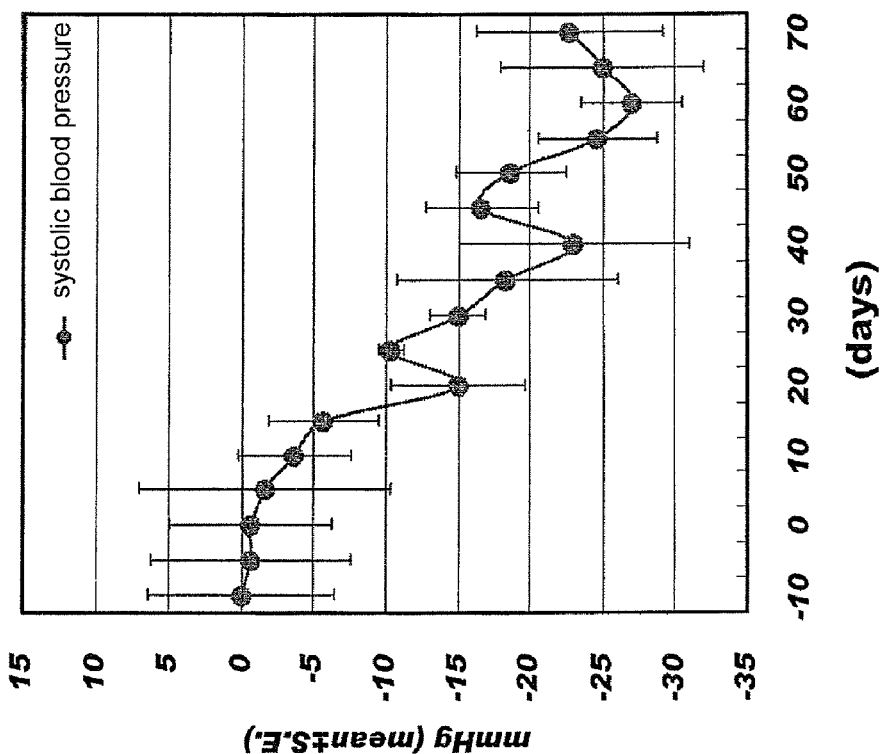
FIG. 6 shows a time-course change in the (a) diastolic blood pressure and in the (b) systolic blood pressure when a composition containing a hot water extract from the carpophore of the strain of turkey tail mushroom (test strain 1, FERM BP-10633) of the present invention was chronically administered to hypertensive patients.
Figure 6:
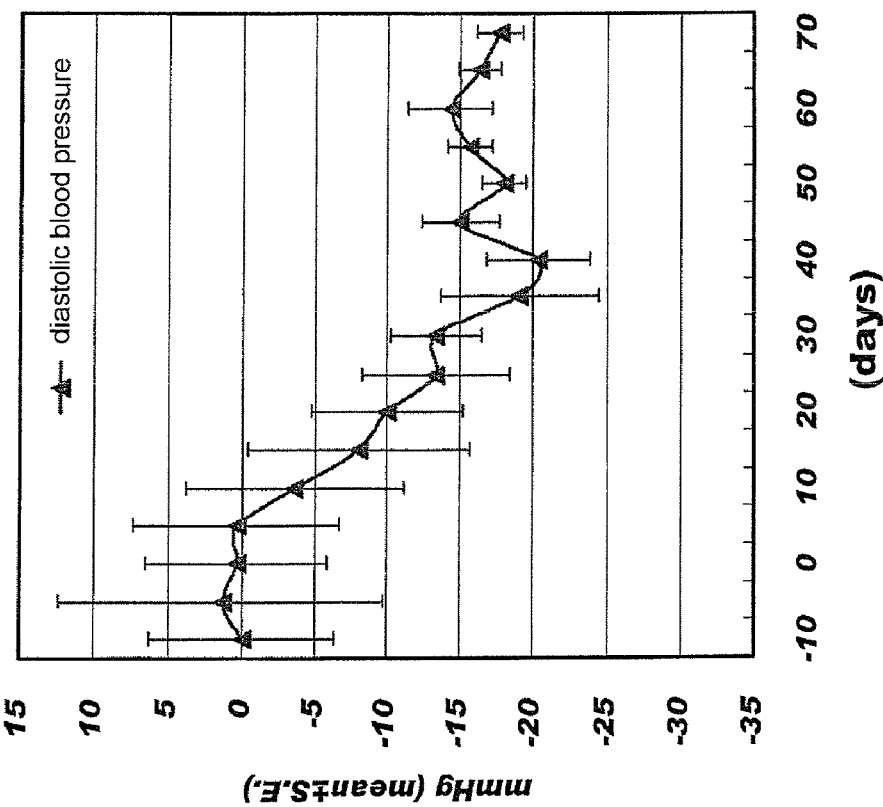

In FIG. 6, the blood pressure of the starting day of administration (day zero) was set at zero, and the variations in the (a) diastolic blood pressure and the (b) systolic blood pressure were plotted every 5 days. The systolic blood pressure started to decrease on the fifth day from the start of administration, and it had a trend to gradually decrease up to the 70th day. The diastolic blood pressure also started to decrease on the tenth day from the start of administration. However, it hardly decreased starting from about the 30th day, and it stabilized and stayed within a fixed range.

From these results, it was suggested that the composition containing turkey tail mushroom extract of the present invention could decrease the blood pressure of hypertensive patients and that there were almost no concerns that the blood pressure might decrease too much even with chronic ingestion.

Figure 7:
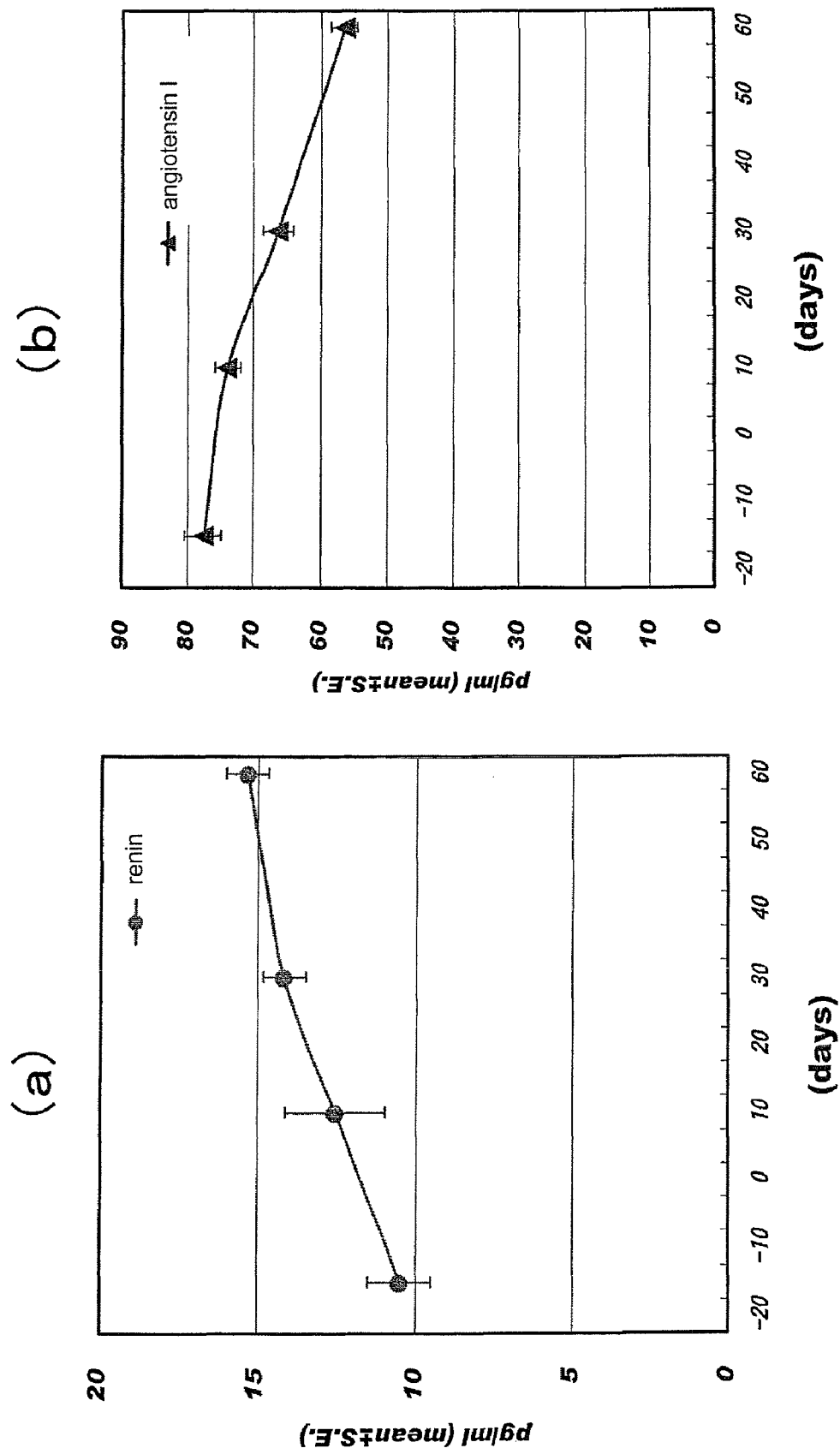
FIG. 7 shows a time-course change in the (a) concentration of renin in blood and in the (b) concentration of angiotensin I in blood when a composition containing a hot water extract from the carpophore of the strain of turkey tail mushroom (test strain 1, FERM BP-10633) of the present invention was chronically administered to hypertensive patients.

In FIG. 7, the variations of the blood renin concentration and the blood angiotensin I concentration are shown for the subjects. With the increase in administered days, the renin concentration increased; on the other hand, the concentration of angiotensin I decreased. Thus, it was suggested that the blood pressure could be controlled without excessive internal secretion of renin, angiotensin, and other hormones into the body or without excessive suppression.

II-4. Immunomodulatory Effect

The immunomodulatory effect was also investigated.

(1) Test Method

The test subjects were 30 healthy adults. The test subjects were requested to orally ingest the health drink of the above-described Formulation Example 2 once every day for 1 month. The amount of intake was 50 mL (200 mg as the powder obtained from a hot water extract of the turkey tail mushroom) per day. Then the ingestion was stopped for 2 months.

Before the start of ingestion, 10 days and 1 month after the start of ingestion, and 2 months after the termination of ingestion, blood of the test subjects was drawn into a blood collection tube containing a blood coagulation inhibitor. The percentages of the immune cells, namely, T cells and NK cells were measured, respectively, by the general clinical test methods.

(2) Results

Figure 8:
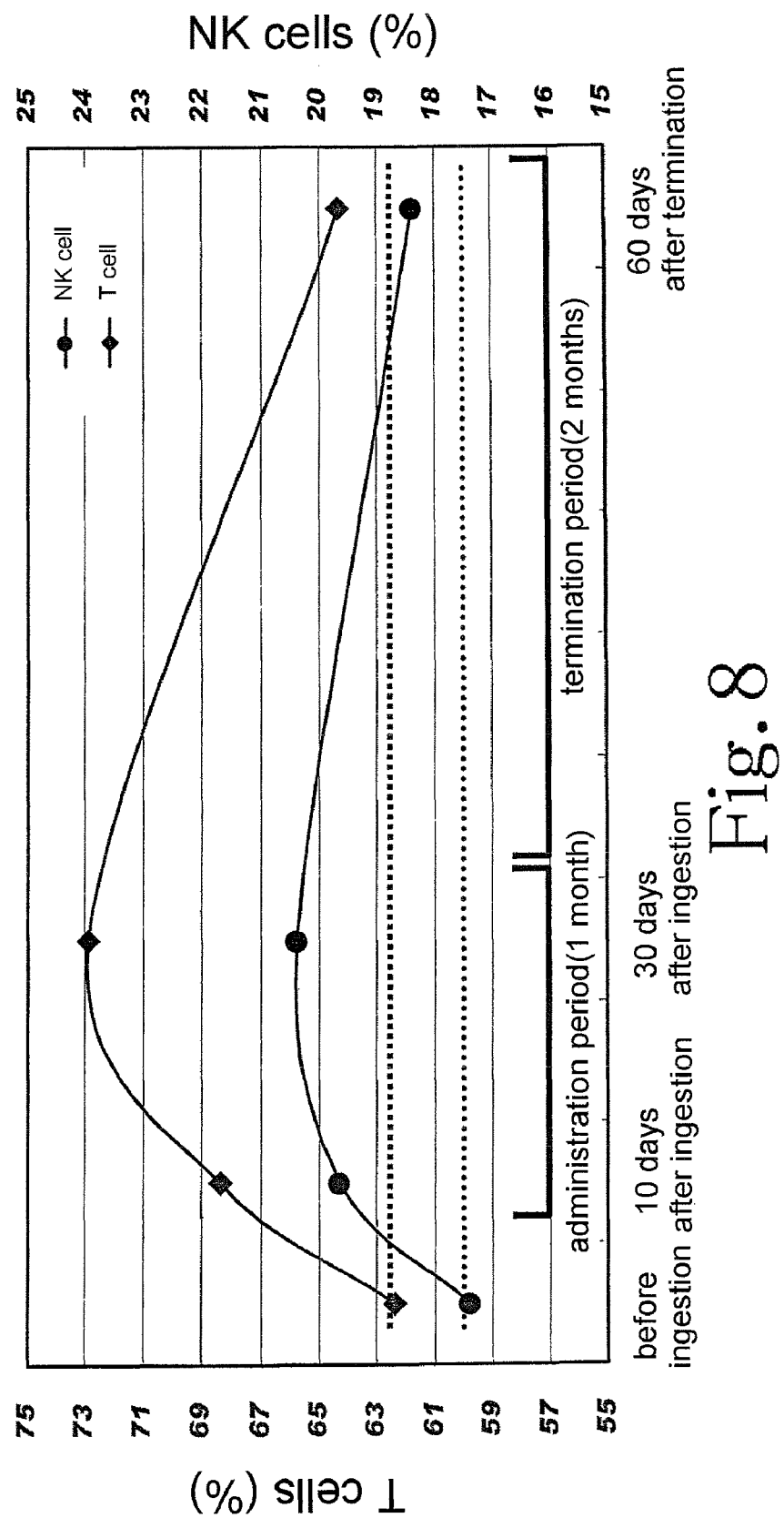
FIG. 8 shows a time-course change in the number of T cells and in the number of NK cells when a composition containing a hot water extract from the carpophore of the strain of turkey tail mushroom (test strain 1, FERM BP-10633) of the present invention was chronically administered to 30 healthy individuals for 1 month and the administration was subsequently stopped for 2 months.

In FIG. 8, the number of T cells (%) and the number of NK cells (%) are shown for the administration period (1 month) and for the subsequent administration termination period (2 months). During the chronic administration period, the number of T cells and the number of NK cells increased with the increase of administered days. After the termination of administration, the number of NK cells and the number of T cells started to decrease. However, a decrease was very mild, and it took 2 months to reach the level before the start of the administration.

Thus, it was suggested that the composition containing the turkey tail mushroom extract of the present invention had an immunostimulating effect and that the sustention of the effect was high by continual ingestion.

What is claimed is:

1. An isolated culture of a strain of turkey tail mushroom (*Trametes versicolor*(L.:Fr.)Pilat), wherein the accession number of the strain is FERM BP-10633.

2. A platelet aggregation inhibitor comprising, as an active component, the turkey tail mushroom culture according to claim 1 and/or its extract.

3. A chemokine gene expression inhibitor comprising, as an active component, the turkey tail mushroom culture according to claim 1 and/or its extract.

4. An antimutagenic agent comprising, as an active component, the turkey tail mushroom culture according to claim 1 and/or its extract.

5. An antitumor agent comprising, as an active component, the turkey tail mushroom culture according to claim 1 and/or its extract.

6. An antihypertensive agent comprising, as an active component, the turkey tail mushroom culture according to claim 1 and/or its extract.

7. An immunomodulatory agent comprising, as an active component, the turkey tail mushroom culture according to claim 1 and/or its extract.

8. A composition for oral use comprising the turkey tail mushroom culture according to claim 1 and/or its extract.

9. The composition for oral use according to claim 8, further comprising one or more selected from the group consisting of microalgae, other basidiomycetes, and extracts thereof.

10. The composition for oral use according to claim 8, wherein the composition is a food or a drink.

11. The composition for oral use according to claim 8, wherein the composition is a pharmaceutical composition.

12. A skin external composition comprising the turkey tail mushroom culture according to claim 1 and/or its extract.

13. The skin external composition according to claim 12, further comprising one or more selected from the group consisting of microalgae, other basidiomycetes, and extracts thereof.

14. A method of treating a tumor, which comprises administering an effective amount of the turkey tail mushroom culture according to claim 1 and/or its extract to a mammal with the tumor.

15. A method of treating hypertension, which comprises administering an effective amount of the turkey tail mushroom culture according to claim 1 and/or its extract to a mammal.

16. A method of maintaining or stimulating immunity, which comprises administering an effective amount of the turkey tail mushroom culture according to claim 1 and/or its extract to a mammal.

17. The composition for oral use according to claim 9, wherein the composition is a food or a drink.

18. The composition for oral use according to claim 9, wherein the composition is a pharmaceutical composition.

* * * * *